US006179782B1

United States Patent
Cucè

(10) Patent No.: US 6,179,782 B1
(45) Date of Patent: Jan. 30, 2001

(54) METHOD AND RELATED APPARATUS FOR MEASURING AND ANALYZING A PHYSICAL QUANTITY OF INTEREST THROUGH THE APPLICATION OF FUZZY LOGIC RULES

(75) Inventor: Antonio Cucè, Messina (IT)

(73) Assignee: STMicroelectronics S.r.l., Agrate Brianza (IT)

( * ) Notice: Under 35 U.S.C. 154(b), the term of this patent shall be extended for 0 days.

(21) Appl. No.: 09/344,736

(22) Filed: Jun. 25, 1999

(51) Int. Cl.⁷ ........................................................ A61B 5/02
(52) U.S. Cl. ...................... 600/481; 600/300; 600/920; 600/923; 600/924; 600/925; 600/898
(58) Field of Search ................................. 600/300, 301, 600/481, 485, 483; 128/897, 898, 920, 922, 923, 924, 925

(56) References Cited

U.S. PATENT DOCUMENTS

| | | | |
|---|---|---|---|
| 4,080,653 | * | 3/1978 | Barnes, Jr. et al. ................. 365/417 |
| 4,320,767 | | 3/1982 | Villa-Real ............................. 128/680 |
| 5,503,624 | | 4/1996 | Roeher et al. .......................... 604/65 |
| 5,584,298 | | 12/1996 | Kabal .................................... 128/672 |
| 5,782,885 | * | 7/1998 | Andersson .............................. 607/17 |
| 5,924,052 | * | 7/1999 | Palm ...................................... 702/71 |
| 6,030,344 | * | 2/2000 | Guracar et al. ....................... 600/447 |

FOREIGN PATENT DOCUMENTS

| | | | |
|---|---|---|---|
| 2 694 421 | 2/1994 | (FR) | ............................... G05B/19/18 |
| WO 94/28481 | 12/1994 | (WO) | ................................. G06F/9/44 |

\* cited by examiner

Primary Examiner—Cary O'Connor
Assistant Examiner—Navin Natnithithadha
(74) Attorney, Agent, or Firm—Theodore E. Galanthay; Robert Iannucci; Seed IP Law Group LLP

(57) ABSTRACT

A method measures and analyzes a physical quantity of interest having first and second significant values dependent on a plurality of characteristic parameters. The method includes storing the characteristic parameters in a storage support external of the measuring device and ancillary thereto; automatically measuring the first and second significant values; and analyzing, on a data processor, the measured significant values to produce a classification thereof based on a knowledge of said characteristic parameters. A system measures and analyzes a physical quantity of interest by application of fuzzy rules. The system comprises an apparatus for measuring the physical quantity of interest having its output connected to a fuzzy processor. The system also comprises a storage support, ancillary to the measuring apparatus, which stores the characteristic parameters of a user being tested, which is connected to a smart card reader/writer in turn connected to the measuring system and the fuzzy processor.

28 Claims, 8 Drawing Sheets

METHOD AND RELATED APPARATUS FOR MEASURING AND ANALYZING A PHYSICAL QUANTITY OF INTEREST THROUGH THE APPLICATION OF FUZZY LOGIC RULES

TECHNICAL FIELD

This invention relates to a method and an apparatus for measuring and analyzing a physical quantity of interest, in particular a blood pressure signal, by the application of fuzzy logic rules.

The invention particularly, but not exclusively, concerns the measurement of arterial blood pressure, and the description hereinbelow will cover this field of application for convenience of illustration.

BACKGROUND OF THE INVENTION

As is well known, the evaluation of arterial pressure represents an essential parameter to the diagnostics of the human body, in both normal and pathological situations.

A significant example of a field where a knowledge of arterial pressure is needed is the prevention of cardio-circulatory diseases.

The measurement of arterial pressure, at one time tied to the attendance by specialized medical personnel equipped with appropriate instruments, can now be carried on "at home", thanks to the availability of automatic pressure measuring devices which are easy to operate and relatively inexpensive.

Accordingly, the number is growing of those who choose to add such automatic blood pressure meters to their domestic first-aid equipment.

Prior art devices can take measurements with varying degrees of accuracy in a short time, and require no special knowledge or skill on the part of their users.

They have an important limitation, however, in that they offer no support for classification of the evidence provided by the pressure readings. Consequently, there exists a risk that they may infuse baseless worry or overconfidence.

The data gathering operations, e.g., for arterial pressure, and attendant classification, e.g., within the clinical picture of each patient, may appear simple at first sight. Actually, these are lengthy, complicated operations contingent on a number of factors. In particular, the arterial pressure signal is dependent on:

the patient's characteristic parameters, such as age, sex, race, possible pathological and/or functional conditions; and parameters tied to local environmental conditions, such as temperature, pressure, possible noise.

SUMMARY OF THE INVENTION

An embodiment of the present invention provides a device for measuring arterial pressure, which can sense and classify data within appropriate ranges that may differ from one clinical picture to another of the various patients undergoing the test. The device includes a measuring system for a physical quantity of interest whose output is connected to a fuzzy processing system.

The apparatus includes a measuring device which can memorize the characteristic parameters of a user undergoing the test, including a possible personalized medical strategy.

In particular, the measuring device is provided with appropriate interfaces for reading characteristic parameters stored up in an external support, ancillary to the measuring device, and provided with suitable processing systems for the measured data on the basis of the characteristic parameters made available to the device, in particular fuzzy processing systems.

In addition, an embodiment of the invention is directed to a method for measuring and analyzing a physical quantity of interest by applying fuzzy logic rules, said quantity having first and second significant values which are dependent on a plurality of characteristic parameters.

Accordingly, this invention is to provide a personalized smart system for measuring arterial pressure in an automatic manner, and subsequently analyzing the readings so as to provide a classification thereof, the classification being based on a knowledge of the patient's characteristic parameters, including any medical directions.

The features and advantages of the measuring/analyzing method and apparatus according to the invention will be apparent from the following description of embodiments thereof, given by way of non-limitative examples with reference to the accompanying drawings.

DETAILED DESCRIPTION

For arterial pressure values to be correctly read and classified on a personal basis, a measuring device is needed which can take account of such basic parameters as are tied to the environmental conditions in which it is operated, and of the characteristic parameters of the individual patient using it.

As to the evaluation of parameters dependent on the environmental conditions in which an automatic pressure measuring device is used, appropriate sensing equipment can be arranged to solve the problem in an efficient manner.

The situation is far more complicated for the characteristic parameters of the patient being tested or end user of the pressure measuring device.

In this case, there are two alternative courses to be followed: either leave it for the user to enter his/her own data every time that he/she takes a pressure reading, or store all such information once into a memory incorporated to the measuring device.

The last-mentioned approach is surely more practical, and would require expanded capabilities of the measuring device, both in terms of storage capacity and the provisions for data processing, if the device is to be used by a panel of users.

Furthermore, the user's characteristic parameters, regardless of how stored, would be difficult to inspect or modify by other people (e.g.,, the family doctor or a specialist), because the modifications would have to be made directly on the measuring device.

And in many cases, a device is needed which can measure and classify pressure readings according to personalized medical directions.

Figure 1:
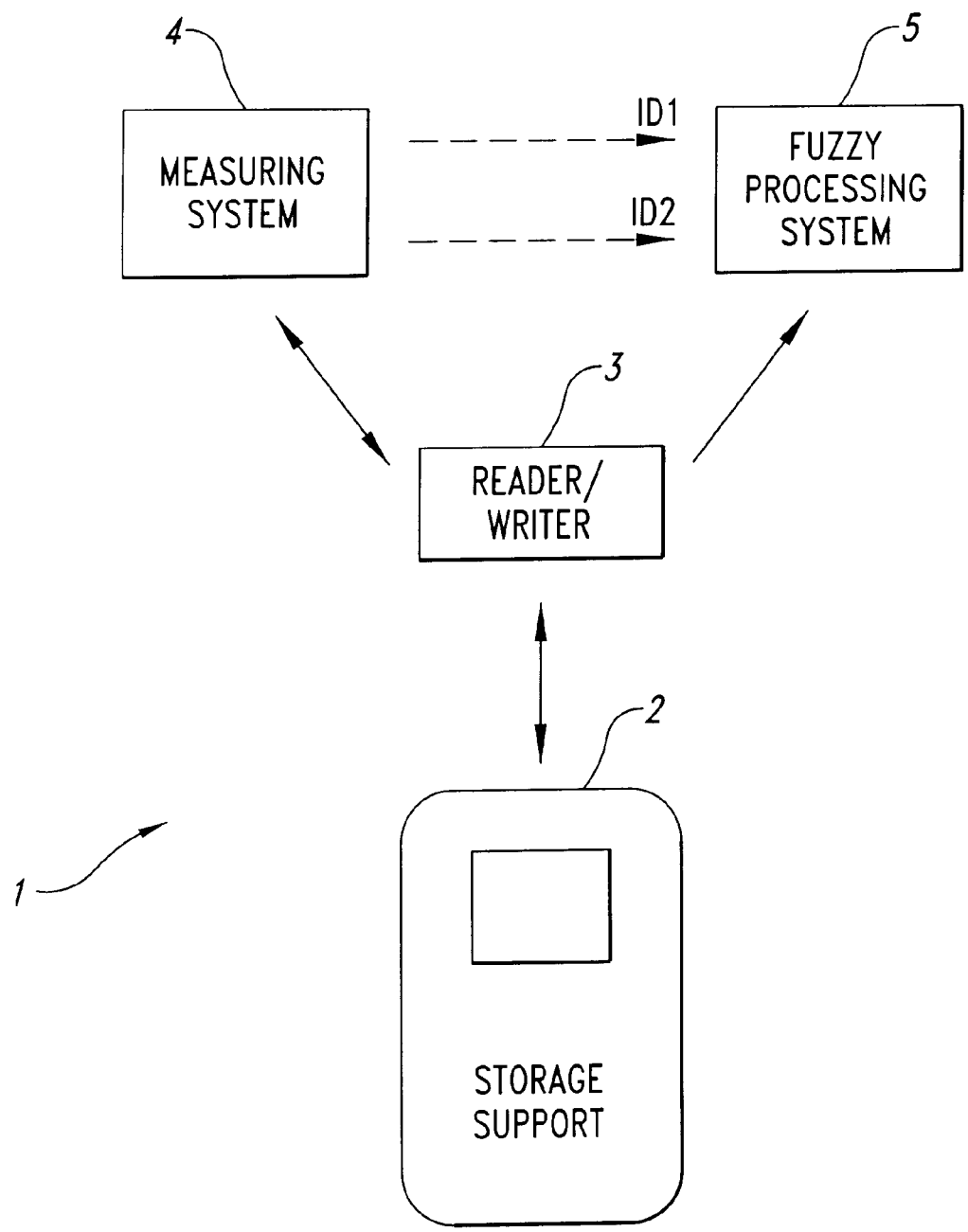
FIG. 1 is a schematic diagram of an apparatus for measuring a quantity of interest according to an embodiment of the invention.
Figure 2:
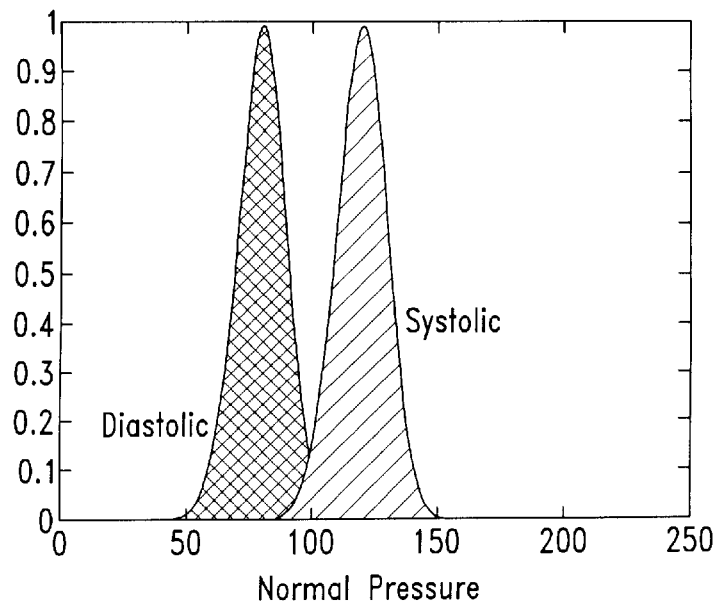
FIG. 2 is a graph of first and second significant values of a quantity of interest, in a normal condition of the patient undergoing the test.
Figure 3:
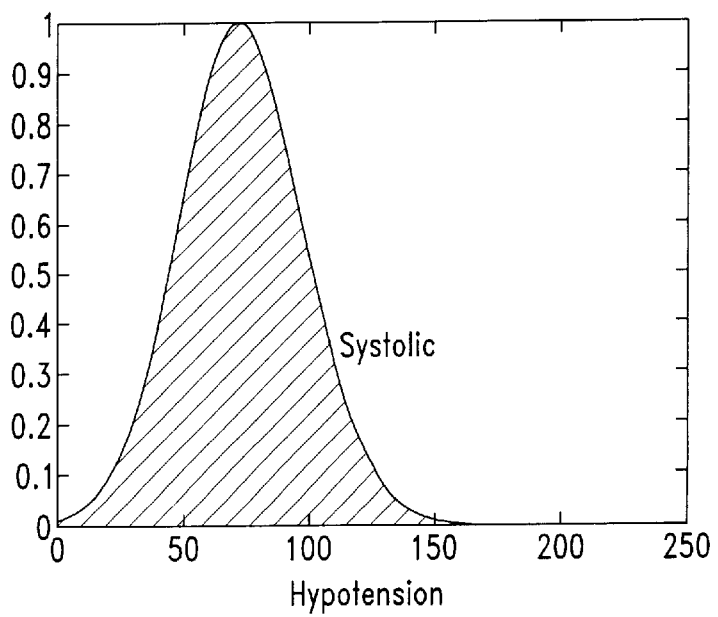
FIGS. 3 to 7 illustrate statistical distributions of the significant values of FIG. 2 under different conditions, in particular different pathological conditions, of the patient undergoing the test.
Figure 4:
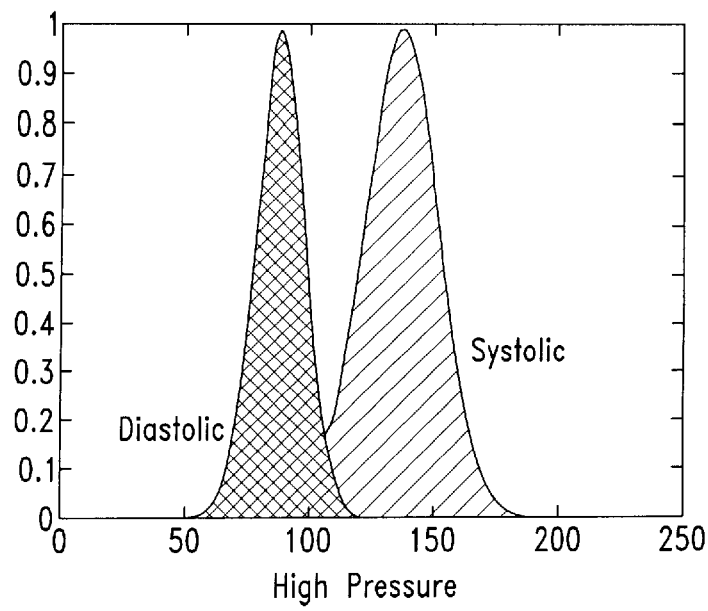
Figure 5:
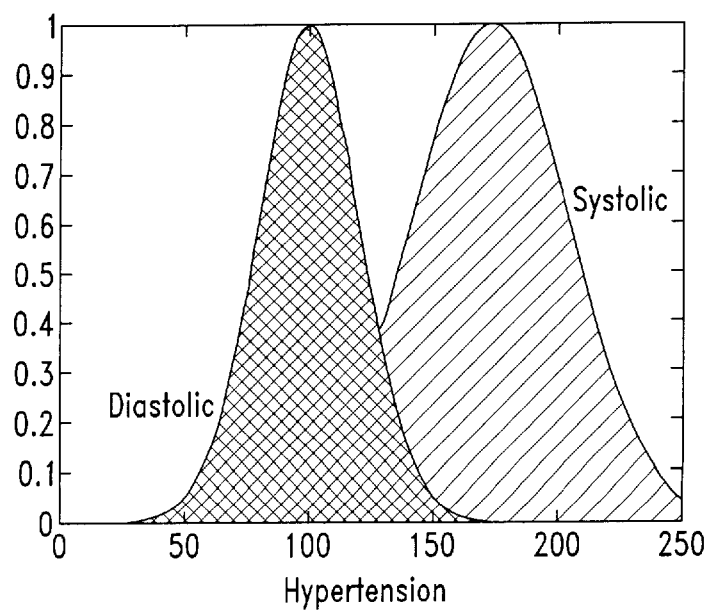
Figure 6:
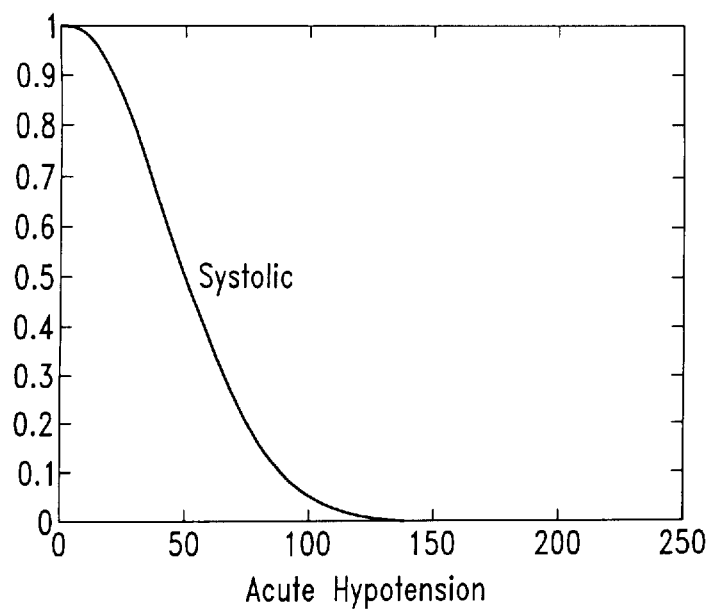
Figure 7:
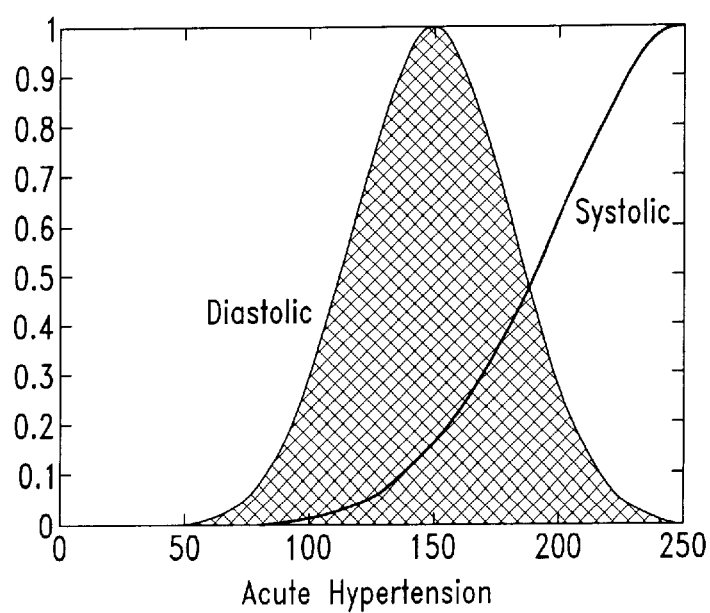
Figure 8:
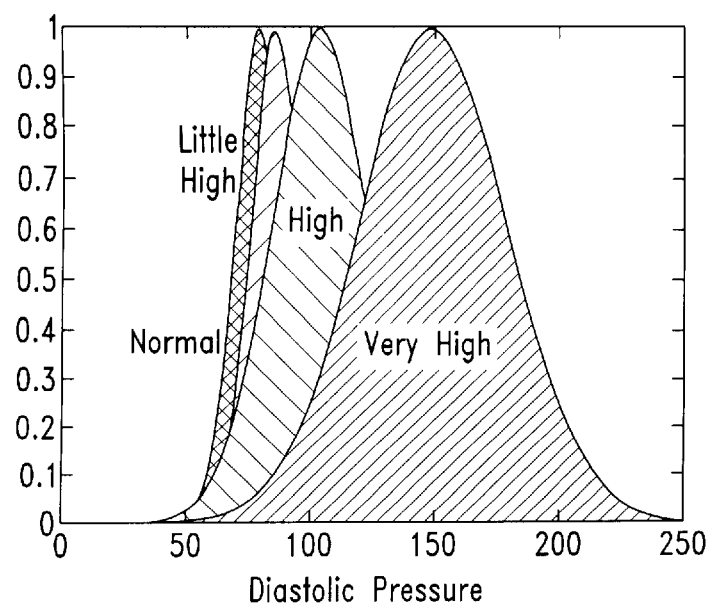
FIG. 8 shows schematically a set of fuzzy membership functions relating to the first significant value of FIG. 2, for a personalized classification of that value.
Figure 9:
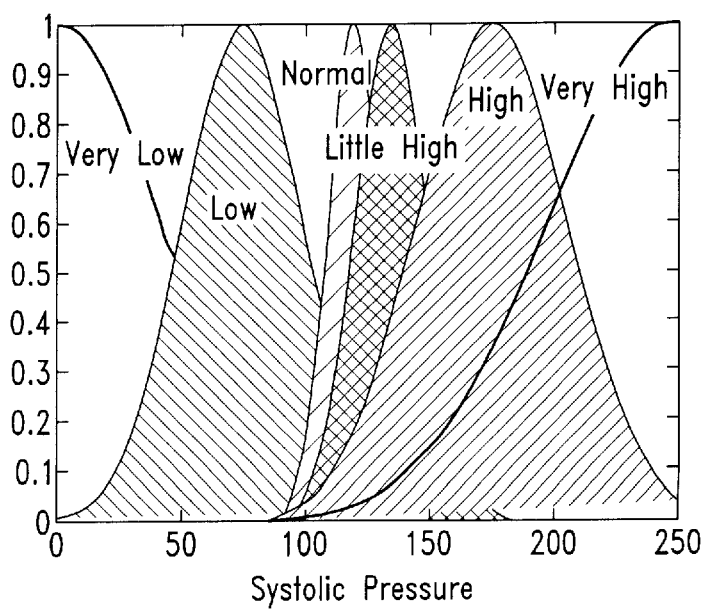
FIG. 9 shows schematically another set of fuzzy membership functions relating to the second significant value of FIG. 2, for a personalized classification of that value.

A measuring and analyzing apparatus 1 is shown schematically in FIG. 1. It represents a personalized smart system for measuring a significant quantity and successively storing, processing and classifying the measured values.

In particular, the apparatus 1 is intended for measuring arterial pressure, and the description that follows will cover this specific field of application for convenience of illustration.

The measuring and analyzing apparatus 1 comprises a storage support 2 containing the characteristic parameters of a user subjected to the test. This storage support 2 serves essentially as a Health Card for the user.

Quite simply, the storage support 2 may be in the form of a smart card, i.e., a card incorporating a microprocessor capable of storing data of interest, in this case the characteristic parameters of a single user and any medical directions for a personalized classification of the measured pressure values.

The characteristic parameters can be expected to include:

Surname, Name(s), Age, Sex, Race, Pregnancy, Weight, Arm circumference, Height, Normal systolic pressure, Normal diastolic pressure, Normal heart beat frequency, readings taken at different times, etc.

The medical directions, with respect to arterial pressure measurements and evaluations, may include:

Normal pressure conditions, Hypotension, High pressure, Hypertension, Acute hypotension, Acute hypertension.

The above-listed conditions correspond to different diagnostic pictures relating to the cardio-circulatory system, and enable the pressure measurement data to be properly classified.

Advantageously, a system of fuzzy rules is provided wherein each rule can identify one of the clinical pictures listed above. In particular, the fuzzy rule system of this invention is based on a plurality of membership functions which are specific to each patient and obtained from measurements taken by specialized personnel, such as a physician or pharmacist, on the basis of significant values of the arterial pressure signal, that is systolic and diastolic pressure values, as illustrated by the graphs shown in FIGS. 2 to 7.

From these graphs, a system of fuzzy rules can be constructed for classifying the arterial pressure data, taking as the membership functions (or terms) the trends of the systolic and diastolic pressures plotted for each patient.

The values of systolic pressure and diastolic pressure can be grouped into a finite number of different ranges, and for each graph, a rule expressed on the terms presented in the graph and tied to the AND logic operator can be created.

In the instance under consideration, the following system of fuzzy rules is obtained:

```
IF  Diastolic_Pressure IS Normal
    AND Systolic_Pressure IS Normal
    THEN Pressure_Normal
IF  Systolic_Pressure IS Low
    THEN Hypotension
IF  Diastolic_Pressure IS Medium_High
    AND Systolic_Pressure IS Medium_High
    THEN High_Pressure
IF  Diastolic_Pressure IS High
    AND Systolic_Pressure IS High
    THEN Hypertension
IF  Diastolic_Pressure IS Very_High
    AND Systolic_Pressure IS Very_High
    THEN Acute_Hypertension
IF  Systolic_Pressure IS Very_Low
    THEN Acute_Hypotension
```

The measuring and analyzing apparatus 1 further includes a smart card reader/writer 3 for a storage support 2 of the smart card type. The smart card type of storage support 2 is, therefore, bi-directionally connected to the reader/writer 3.

This reader/writer 3 is structured to receive a storage support 2 of the smart card type, and is connected to a heart beat frequency and blood pressure measuring system 4, and to a fuzzy processing system 5 of the fuzzy pressure analyzer type, specifically to implement the aforementioned fuzzy rules.

It should be noted that the reader/writer 3 is, therefore, connected bi-directionally to the measuring system 4 and uni-directionally to the fuzzy processing system 5.

The measuring system 4 is capable of detecting in a smart fashion the values of the arterial pressure and heart beat frequency signals. Advantageously, the measuring system 4 includes an automatic device for measuring the arterial pressure signal, based on appropriate sets of fuzzy rules derived from statistical trends of that signal, and includes devices for calculating the values of heart beat frequency, systolic pressure, and diastolic pressure.

A preferred embodiment of this measuring system 4 is described in U.S. patent application Ser. No. 09/193,527, filed on Nov. 17, 1998, assigned to STMicroelectronics S.r.l, and incorporated hereto by reference.

Figure 13:
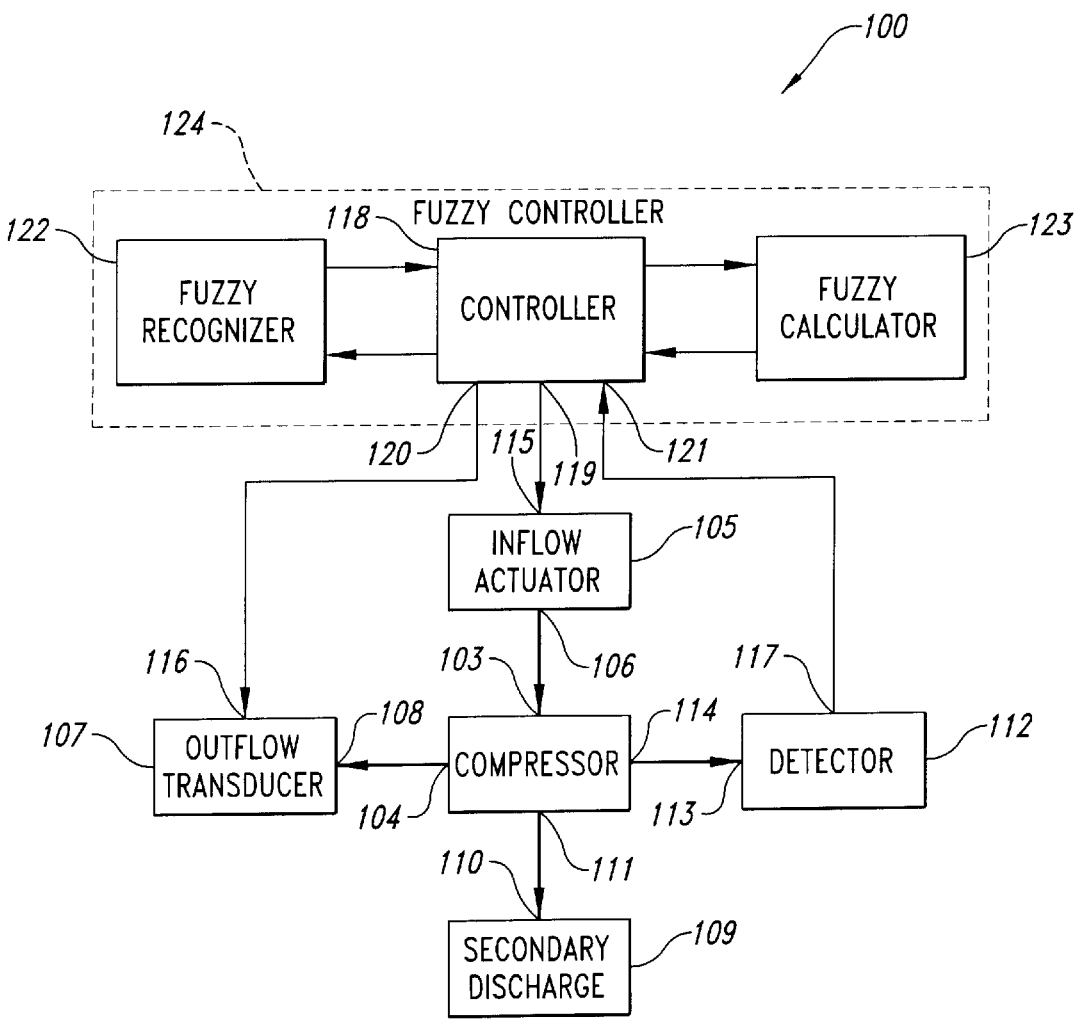
FIG. 13 is a schematic block diagram of a preferred embodiment of a measuring system adapted for use with the apparatus of FIG. 1.

In particular, shown diagrammatically in FIG. 13 is a measuring system 100 adapted for use as the measuring system associated with the measuring and analyzing apparatus 1 according to the invention. The measuring system 100 comprises a plurality of functional blocks, as follows:

A compressor block 102 comprising, in particular, a conventional inflatable armband.

The compressor block 102 has a first inlet 103 which corresponds essentially to a physical opening in the armband through which the armband can be inflated, and a first outlet 104 corresponding, similarly as the first inlet 103, to a physical opening, but through which the armband can be deflated.

This compressor block 102 is arranged to compress a portion of a limb which contains the artery from which the reading is to be taken and has the inflatable armband suitably fitted around it.

An inflow actuator block 105 comprising an air-blowing device, specifically a conventional pump.

The inflow actuator block 105 has an outlet 106 connected to the first inlet 103 of the compressor block 102, and is utilized to inflate the inflatable armband.

An outflow transducer block 107 including a quick air-exhausting device, e.g., a conventional valve.

The outflow transducer block 107 has an inlet 108 connected to the first outlet 104 of the compressor block 102, and is operative to deflate the inflatable armband.

A secondary discharge block 109 having an inlet 110 connected to a second outlet 111 of the compressor block 102.

This secondary discharge block 109 includes a device for exhausting air at a near-constant slow rate, specifically a pin.

A detector block 112 comprising, in particular, an electronic pressure detecting/measuring device, such as a conventional pressure sensor.

The detector block 112 has an inlet 113 connected to a second outlet 114 of the compressor block 102. It should be noted that the pressure sensor in the detector block 112 is adapted to measure the air pressure inside the inflatable armband of the compressor block 102.

A controller block 118, specifically a regulator of the air inflow and outflow to/from the inflatable armband, arranged to act on the pump contained in the inflow actuator block 105 and on the valve contained in the outflow transducer block 107.

The controller block 118 has a first output 119 connected to a first enable input 115 of the inflow actuator block, a second output 120 connected to a second enable input 116 of the outflow transducer block 107, and an input 121 connected to a control output 117 of the detector block 112.

In particular, the controller block 118 delivers, on the outputs 119 and 120, respective signals to activate (and deactivate) the intake/discharge of air to/from the pump and the valve contained in the blocks 105 and 107. These activation signals can be simple on/off electric signals.

The controller block 118 also receives, on the input 121, a control signal from the pressure sensor of the detector block 112.

A fuzzy recognizer block 122, particularly for detecting the heart beat and comprising a first fuzzy processing device which implements a first system of fuzzy rules, hereinafter referred to as system FUZZY 1.

The fuzzy recognizer block 122 is connected bi-directionally to the controller block 118.

A fuzzy calculator block 123 comprising a second processing device which implements a second system of fuzzy rules, hereinafter referred to as system FUZZY 2.

The fuzzy calculator block 123 is also connected two-directionally to the controller block 118.

In essence, the measuring system 100 shown in FIG. 13 produces a compression on a limb, and hence of the artery therein on which the reading is to be taken. This compression is achieved through the combined use of the compressor block 102, the inflow actuator block 105, and the outflow transducer block 107 (or precisely, of the pump and the valve incorporated to said actuator and transducer blocks).

The measuring system 100 also allows the amount of compression generated to be adjusted by means of the pressure sensor in the detector block 112, and of a fuzzy controller 124 which comprises the controller block 118, and the fuzzy recognizer 122 and fuzzy calculator 123 blocks.

The fuzzy controller 124 detects the existence of the heart beat, thereby allowing the significant values of the blood pressure signal, i.e., the systolic and diastolic pressure values, to be found.

Advantageously, a measuring system 4, constructed similar to the measuring system disclosed in the aforementioned U.S. Patent Application (to which reference can be had for a more detailed description of the system and its operation), can utilize, instead of generic statistic data about the distribution of the systolic and diastolic pressure values, normal or average data, specific to the user and contained in its storage support 2, thereby optimizing in particular the method of calculating the systolic and diastolic pressure values used in a current arterial pressure measuring operation.

The processing system 5 likewise comprises a device for processing sets of fuzzy rules. In particular, these rules may be supplied from a memory area located either within or without the processing system 5.

Advantageously, the input data ID1, ID2 to the processing system 5 are the systolic and diastolic pressure values (maximum & minimum blood pressures), and the frequency values of the heart beat as measured on the measuring system 4 against the data stored in the storage support 2.

In fact, the measuring system 4 uses data from the storage support 2 (which data can be personalized according to the user's characteristic parameters and any medical directions) and makes the sensed values of systolic pressure, diastolic pressure, and heart beat frequency available to the reader/writer 3 and the processing system 5.

This processing system 5 may include a processor adapted to process a set of fuzzy rules stored in the storage support 2 for classifying the pressure values sensed by the measuring system 4 on the basis of personal statistic records, also stored in the storage support 2.

Advantageously, it can be arranged for the processing system 5 to use, lacking such personal statistic records, its own stored rules to provide a classification of the pressure values based on default statistic records pre-entered in the storage support 2 of the smart card type.

Figure 10:
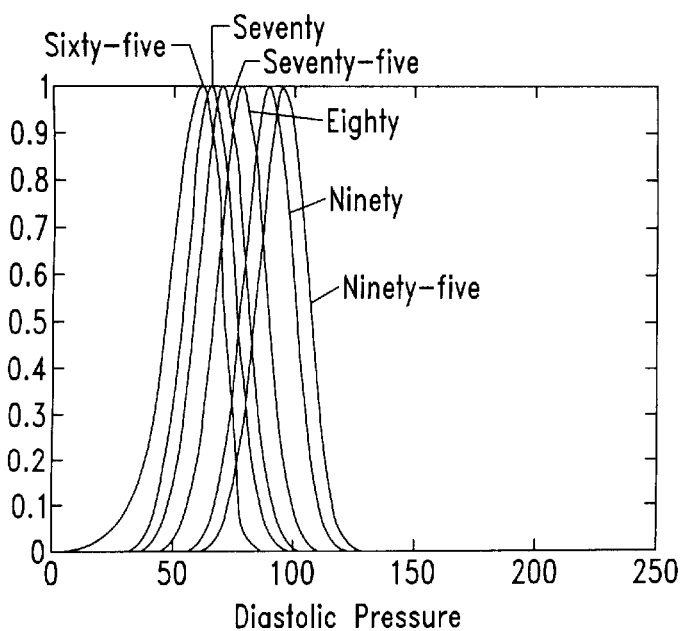
FIGS. 10, 11 and 12 show schematically sets of fuzzy membership functions relating to said first and second significant values in FIG. 2, for a personalized classification of such values.
Figure 11:
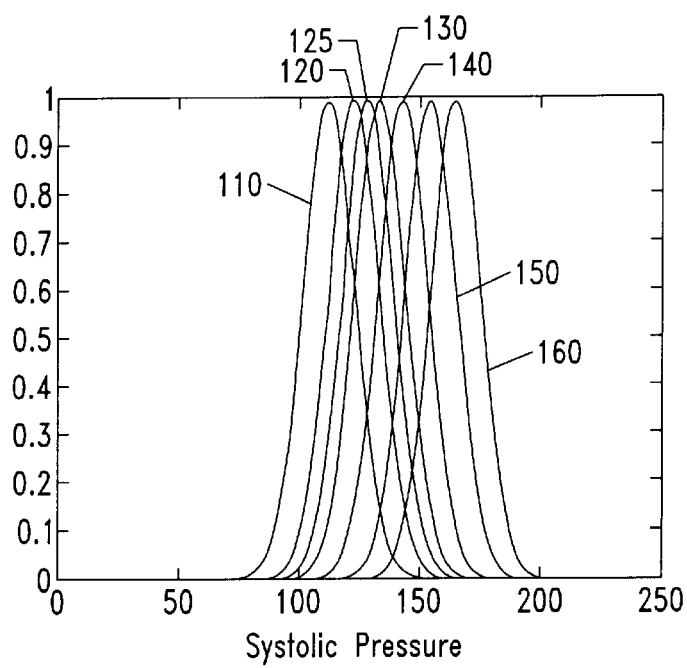
Figure 12:
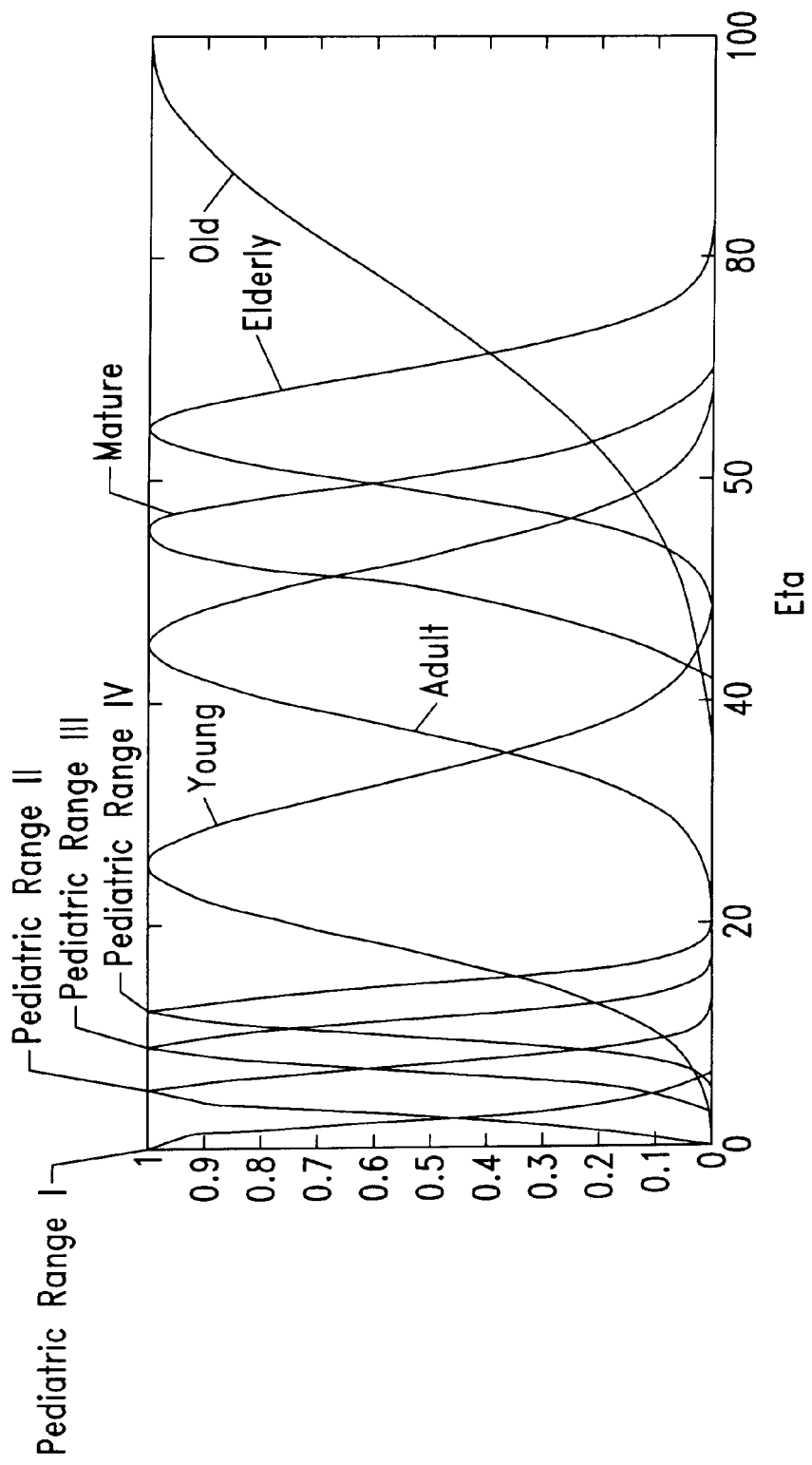

An example of fuzzy rules for a general classification of the pressure values is discussed herein below and graphically outlined in FIG. 12. Specifically, this system of fuzzy rules provides a definition of "Normal", that is of a non-pathological condition of the patient according to age, on the grounds of measured values of diastolic pressure and systolic pressure, as shown in FIGS. 10 and 11.

```
IF Age IS Pediatric_Range_I
    AND Diastolic_Pressure IS 65
    AND Systolic_Pressure IS 110
    THEN Normal
IF Age IS Pediatric_Range_II
    AND Diastolic_Pressure IS 70
    AND Systolic_Pressure IS 120
    THEN Normal
IF Age IS Pediatric_Range_III
    AND Diastolic_Pressure IS 80
    AND Systolic_Pressure IS 125
    THEN Normal
IF Age IS Pediatric_Range_IV
    AND Diastolic_Pressure IS 80
    AND Systolic_Pressure IS 140
    THEN Normal
IF Age IS Young
    AND Diastolic_Pressure IS 70
    AND Systolic_Pressure IS 130
    THEN Normal
IF Age IS Adult
    AND Diastolic_Pressure IS 80
    AND Systolic_Pressure IS 140
    THEN Normal
IF Age IS Mature
    AND Diastolic_Pressure IS 90
    AND Systolic_Pressure IS 150
    THEN Normal
IF Age IS Elderly
    AND Diastolic_Pressure IS 90
    AND Systolic_Pressure IS 170
    THEN Normal
IF Age IS Old
    AND Diastolic_Pressure IS 95
    AND Systolic_Pressure IS 140
    THEN Normal
```

Finally, it should be noted that, whereas the phase of reading the data stored in the storage support 2 can be activated by the measuring system 4 and the processing system 5 through the reader/writer, the data writing phase can be activated only by the measuring system 4 (by one-way connection of the reader/writer 3 and the processing system 5, and two-way connection of the read/write device 3 and the measuring system 4).

To summarize, the measuring and analyzing apparatus 1 affords a number of advantages.

In the first place, the apparatus 1 can measure the pressure values of any patients in an efficient manner.

Based on the information stored in the storage support 2 of the smart card type and relating to average or normal pressure values of the patient in question, non-traumatizing measurements can be taken, from either the duration standpoint and that of the maximum pressure value attained.

In addition, with the apparatus 1 it becomes possible and extremely simple to store the measured values on a physical support (specifically, the smart card type of storage support 2) which can be easily taken away to enable other persons, such as one's family doctor, to analyze the values directly.

Advantageously, compared to conventional devices, the apparatus 1 introduces a flexible phase of classifying the measured data which provides a personalized classification of the measured arterial pressure values on the basis of the tested patient's own parameters and medical directions, or alternatively provides an equally useful default classification based on general statistic trends of the values under consideration.

Thus, the apparatus 1 fits perfectly in the expanding perspective of having all the health curriculum information gathered within a storage support 2, such as a smart card, thereby to create regular "Health Cards" as stated before. Proposals for study have already been submitted by some countries of the European Union, among which Belgium.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for measuring and analyzing a physical quantity of interest having first and second significant values dependent on a plurality of characteristic parameters, the method comprising:

storing said characteristic parameters in a storage support external of the measuring device and ancillary thereto, said characteristic parameters including diagnostic pictures of a user being tested;

automatically measuring said first and second significant values;

reading said characteristic parameters from the storage support; and classifying the measured significant values by analyzing, on a data processor, the measured significant values based on said characteristic parameters read from the storage support.

2. A measuring and analyzing method according to claim 1, wherein the characteristic parameters include parameters dependent on environmental conditions existing while the significant values are being measured, and on significant data of the user being tested.

3. A measuring and analyzing method according to claim 2, wherein said significant data of the user being tested is clinical data comprising:

Surname, Name(s), Age, Sex, Race, Pregnancy, Weight, Arm circumference, Height, Normal systolic pressure, Normal diastolic pressure, Normal heart beat frequency, and readings taken at different times.

4. A measuring and analyzing method according to claim 3, wherein said significant data of the user being tested further includes medical directions for a personalized classification of the measured values.

5. A measuring and analyzing method according to claim 1, characterized in that a system of fuzzy rules is used wherein each rule allows a different diagnostic picture of the user to be identified.

6. A measuring and analyzing method according to claim 5, characterized in that said system of fuzzy rules comprises a plurality of membership functions that are specific to each user and derived from measurements made in consideration of the significant values of the quantity of interest.

7. A measuring and analyzing method according to claim 1, wherein said analyzing step includes analyzing the significant values based on fuzzy logic rules.

8. A measuring and analyzing method according to claim 1, wherein:

said physical quantity of interest is arterial blood pressure; and said first and second significant values correspond to diastolic and systolic pressures, respectively.

9. A measuring and analyzing method according to claim 8, wherein said diagnostic pictures are related to the cardiocirculatory system of the user and include the following conditions:

Normal pressure conditions, Hypotension, High pressure, Hypertension, Acute hypotension, Acute hypertension.

10. A measuring and analyzing method according to claim 8 wherein membership functions are obtained as rules expressed on the basis of the values relating to systolic pressure and diastolic pressure tied to the AND logic operator.

11. A measuring and analyzing method according to claim 10, wherein the following system of fuzzy rules is used during the classifying step:

```
IF   Diastolic_Pressure IS Normal
     AND Systolic_Pressure IS Normal
     THEN Pressure_Normal
IF   Systolic_Pressure IS Low
     THEN Hypotension
IF   Diastolic_Pressure IS Medium_High
     AND Systolic_Pressure IS Medium_High
     THEN High_Pressure
IF   Diastolic_Pressure IS High
     AND Systolic_Pressure IS High
     THEN Hypertension
IF   Diastolic_Pressure IS Very_High
     AND Systolic_Pressure IS Very_High
     THEN Acute_Hypertension
IF   Systolic_Pressure IS Very_Low
     THEN Acute_Hypotension
``` where:

Systolic_Pressure and Diastolic_Pressure are the measured values for the systolic pressure and the diastolic pressure of the user;

Normal, Low, Medium_High, High, Very_High and Very_Low are membership functions into which the measured pressure values are classifying into a plurality of fuzzy sets; and Pressure_Normal, Hypotension, High_Pressure, Hypertension, Acute_Hypertension and Acute_ Hypotension are membership values of the measured pressure values and correspond to different diagnostic pictures.

12. A measuring and analyzing method according to claim 11, wherein, lacking personal statistic records, a system of fuzzy rules based on default statistic records is used to provide a classification of the pressure values.

13. A measuring and analyzing method according to claim 12, wherein the following system of fuzzy rules based on default statistic records is used:

```
IF Age IS Pediatric_Range_I
    AND Diastolic_Pressure IS 65
    AND Systolic_Pressure IS 110
    THEN Normal
IF Age IS Pediatric_Range_II
    AND Diastolic_Pressure IS 70
    AND Systolic_Pressure IS 120
    THEN Normal
IF Age IS Pediatric_Range_III
    AND Diastolic_Pressure IS 80
    AND Systolic_Pressure IS 125
    THEN Normal
IF Age IS Pediatric_Range_IV
    AND Diastolic_Pressure IS 80
    AND Systolic_Pressure IS 140
    THEN Normal
IF Age IS Young
    AND Diastolic_Pressure IS 70
    AND Systolic_Pressure IS 130
    THEN Normal
IF Age IS Adult
    AND Diastolic_Pressure IS 80
    AND Systolic_Pressure IS 140
    THEN Normal
IF Age IS Mature
    AND Diastolic_Pressure IS 90
    AND Systolic_Pressure IS 150
    THEN Normal
IF Age IS Elderly
    AND Diastolic_Pressure IS 90
    AND Systolic_Pressure IS 170
    THEN Normal
IF Age IS Old
    AND Diastolic_Pressure IS 95
    AND Systolic_Pressure IS 140
    THEN Normal
``` where:
Age is a characteristic parameter corresponding to the patient's age:
Pediatric_Range_I, Pediatric_Range_II, Pediatric_Range_III, Pediatric_Range_IV, Young, Adult, Mature, Elderly, and Old are membership functions dividing the variations of the Age parameter into a plurality of fuzzy sets;

Sixty_Five, Seventy, Eighty, Ninety, Ninety_Five, One_Hundred_and_Ten One_Hundred_and_Twenty, One_Hundred_and_Twenty_Five, One_Hundred_and_Thirty, One_Hundred_and Forty, One_Hundred_and_Fifty, and One_Hundred_and_Seventy are membership functions dividing the variations of the measured pressure values into plural fuzzy sets; and Normal is the membership value of the measured pressure values which corresponds to a non-pathological condition of the user.

14. A system for measuring and analyzing a physical quantity of interest by the application of fuzzy rules, said quantity having at least first and second significant values dependent on a plurality of characteristic parameters, the system comprising:

a measuring apparatus structured to measure the significant values of the physical quantity of interest;

a storage support, ancillary to the measuring apparatus and containing the characteristic parameters of a current user being tested;

a storage support reader/writer connected to the measuring apparatus and structured to read from and write to the storage support; and a fuzzy processor coupled to the measuring apparatus and storage support, the fuzzy processor being structured to use a system of fuzzy rules wherein each rule allows a different user's diagnostic picture to be identified.

15. A measuring and analyzing system according to claim 14, wherein the storage support reader/writer includes a smart card reader/writer structured to receive a storage support of the smart card type using a two-directional connection.

16. A measuring and analyzing system according to claim 14, wherein the smart card reader/writer is connected two-directionally to the measuring apparatus and one-directionally to the fuzzy processor, such that the measuring apparatus and processing system can both activate a phase of data reading from the storage support through the smart card reader/writer, whereas a phase of writing in such data can only be activated by the measuring apparatus.

17. A measuring and analyzing system according to claim 14, wherein the storage support stores clinical data of the current user which includes:

Surname, Name(s), Age, Sex, Race, Pregnancy, Weight, Arm circumference, Height, Normal systolic pressure, Normal diastolic pressure, Normal heart beat frequency, and readings taken at different times, wherein the fuzzy processor is structured to use the clinical data to classify the measured significant values.

18. A measuring and analyzing system according to claim 14, wherein the storage support stores medical directions corresponding to different diagnostic pictures of the current user being tested and the fuzzy processor is structured to classify the measured significant values using the medical directions.

19. A measuring and analyzing system according to claim 14, wherein said system of fuzzy rules comprises a plurality of membership functions which are specific to each user and derived from measurements of the physical quantity of interest made by said measuring apparatus, taking account of the significant values of the quantity of interest.

20. A measuring and analyzing system according to claim 14 wherein:

said physical quantity of interest is the arterial blood pressure of the current user; and said first and second significant values correspond to the diastolic and systolic pressure values of the arterial blood pressure, respectively.

21. A measuring and analyzing system according to claim 20, wherein the measuring apparatus is structured to measure the arterial blood pressure and the heart beat frequency of the current user using an automatic device that calculates the arterial blood pressure based on appropriate sets of fuzzy rules derived from statistic trends of measured significant values.

22. A measuring and analyzing system according to claim 14, wherein the fuzzy processor uses the following system of fuzzy rules:

```
IF  Diastolic_Pressure IS Normal
    AND Systolic_Pressure IS Normal
    THEN Pressure_Normal
IF  Systolic_Pressure IS Low
    THEN Hypotension
IF  Diastolic_Pressure IS Medium_High
    AND Systolic_Pressure IS Medium_High
    THEN High_Pressure
IF  Diastolic_Pressure IS High
    AND Systolic_Pressure IS High
    THEN Hypertension
IF  Diastolic_Pressure IS Very_High
    AND Systolic_Pressure IS Very_High
    THEN Acute_Hypertension
IF  Systolic_Pressure IS Very_Low
    THEN Acute_Hypotension
``` where:
Systolic_Pressure and Diastolic_Pressure are the measured values for the systolic pressure and the diastolic pressure of a single user;
Normal, Low, Medium_High, High, Very_High and Very_Low are membership functions dividing the variations of the measured pressure value into a plurality of fuzzy sets; and
Pressure Normal, Hypotension, High_Pressure, Hypertension, Acute_Hypertension and Acute_Hypotension are membership values of the measured pressure value which correspond to different diagnostic pictures.

23. A measuring and analyzing system according to claim 22, wherein the fuzzy processor is structured to look for personal statistic records on the storage support and, if none are found, uses the following system of fuzzy rules based on default statistic records, to define a non-pathological condition of the patient:

```
IF Age IS Pediatric_Range_I
    AND Diastolic_Pressure IS 65
    AND Systolic_Pressure IS 110
    THEN Normal
IF Age IS Pediatric_Range_II
    AND Diastolic_Pressure IS 70
    AND Systolic_Pressure IS 120
    THEN Normal
IF Age IS Pediatric_Range_III
    AND Diastolic_Pressure IS 80
    AND Systolic_Pressure IS 125
    THEN Normal
IF Age IS Pediatric_Range_IV
    AND Diastolic_Pressure IS 80
    AND Systolic_Pressure IS 140
    THEN Normal
IF Age IS Young
    AND Diastolic_Pressure IS 70
    AND Systolic_Pressure IS 130
    THEN Normal
IF Age IS Adult
    AND Diastolic_Pressure IS 80
    AND Systolic_Pressure IS 140
    THEN Normal
IF Age IS Mature
    AND Diastolic_Pressure IS 90
    AND Systolic_Pressure IS 150
    THEN Normal
```

-continued

```
IF Age IS Elderly
    AND Diastolic_Pressure IS 90
    AND Systolic_Pressure IS 170
    THEN Normal
IF Age IS Old
    AND Diastolic_Pressure IS 95
    AND Systolic_Pressure IS 140
    THEN Normal
``` where:
Age is a characteristic parameter corresponding to the patient's age:

Pediatric_Range_I, Pediatric_Range_II, Pediatric_Range_III,

Pediatric_Range_IV, Young, Adult, Mature, Elderly and Old are membership functions dividing the variations of the Age parameter into a plurality of fuzzy sets;
Systolic_Pressure and Diastolic_Pressure are the measured values for the systolic pressure and the diastolic pressure of a single user;

Sixty_Five, Seventy, Eighty, Ninety, Ninety_Five, One_Hundred_and_Ten One_Hundred_and_Twenty, One_Hundred_and_Twenty_Five, One_Hundred_and_Thirty, One_Hundred_and_Forty, One_Hundred_and_Fifty, One_Hundred_and_Seventy are membership functions dividing the variations of the measured pressure value into a plurality of fuzzy sets; and
Normal is the membership value of the measured pressure signal which corresponds to a non-pathological condition of the patient.

24. A system for measuring and analyzing a physical quantity of a current user by the application of fuzzy rules, the system comprising:
a measuring apparatus structured to measure the significant values of the physical quantity of interest;
a storage support, ancillary to the measuring apparatus and containing the characteristic parameters of the current user being tested and statistical information of other people related to the physical quantity;
a storage support reader to read the characteristic parameters and statistical information from the storage support; and
a fuzzy processor coupled to the measuring apparatus and storage support, the fuzzy processor being structured to use a system of fuzzy rules structured to classify the physical quantity of the current user based on the significant values measured and on the characteristic parameters and the statistical information read from the storage support.

25. The system of claim 24 wherein the storage support reader includes a smart card reader/writer structured to receive a storage support of the smart card type using a two-directional connection.

26. The system of claim 25, wherein the smart card reader/writer is connected two-directionally to the measuring apparatus and one-directionally to the fuzzy processor, such that the measuring apparatus and processing system can both activate a phase of data reading from the storage support through the smart card reader/writer, whereas a phase of writing in such data can only be activated by the measuring apparatus.

27. A measuring and analyzing apparatus according to claim 24, wherein the storage support stores medical directions corresponding to different diagnostic pictures of the current user being tested and the fuzzy processor is structured to classify the measured significant values using the medical directions.

28. The system of claim 14, wherein said system of fuzzy rules comprises a plurality of membership functions that are specific to the current user and derived from measurements of the physical quantity made by said measuring apparatus, taking account of the significant values of the physical quantity.

\* \* \* \* \*

UNITED STATES PATENT AND TRADEMARK OFFICE
CERTIFICATE OF CORRECTION

PATENT NO.   : 6,179,782 B1
DATED        : January 30, 2001
INVENTOR(S)  : Antonio Cucè

It is certified that error appears in the above-identified patent and that said Letters Patent is hereby corrected as shown below:

<u>Title page,</u>
Item [30], the Foreign Application Priority Data, should read as
-- June 26, 1998 (EP) . . . . . . . 98830387.1 --.

Signed and Sealed this

Twentieth Day of August, 2002

*Attest:*

*Attesting Officer*

JAMES E. ROGAN
*Director of the United States Patent and Trademark Office*